US009220566B2

(12) United States Patent
Schwertner et al.

(10) Patent No.: US 9,220,566 B2
(45) Date of Patent: Dec. 29, 2015

(54) FLUID COLLECTION APPARATUS

(71) Applicant: SG Orthodrape, LLC, Georgetown, TX (US)

(72) Inventors: Charles Schwertner, Georgetown, TX (US); Jinesh Patel, Georgetown, TX (US)

(73) Assignee: SG Orthodrape, LLC, Georgetown, TX (US)

( * ) Notice: Subject to any disclaimer, the term of this patent is extended or adjusted under 35 U.S.C. 154(b) by 368 days.

(21) Appl. No.: 13/663,252

(22) Filed: Oct. 29, 2012

(65) Prior Publication Data

US 2013/0112212 A1 May 9, 2013

Related U.S. Application Data

(60) Provisional application No. 61/552,254, filed on Oct. 27, 2011.

(51) Int. Cl.
*A61B 19/08* (2006.01)
*A61B 19/12* (2006.01)

(52) U.S. Cl.
CPC ............ *A61B 19/12* (2013.01); *A61B 19/088* (2013.01); *A61B 2019/086* (2013.01)

(58) Field of Classification Search
CPC ...... A61B 19/08; A61B 19/38; A61F 15/006; A61M 1/00; A61M 1/0056; A61M 2202/0014; A61M 2202/08; A61M 25/0105; A61M 25/0147; A61M 1/0033; A61M 1/0058; A61M 1/008; A61M 1/0088
USPC .................................................. 128/849–856
See application file for complete search history.

(56) References Cited

U.S. PATENT DOCUMENTS

| | | | | |
|---|---|---|---|---|
| 4,974,604 A * | 12/1990 | Morris | ........................... | 128/853 |
| 5,143,091 A * | 9/1992 | Patnode et al. | ............... | 128/853 |
| 5,419,343 A * | 5/1995 | Taylor | ........................... | 128/849 |
| 5,494,050 A * | 2/1996 | Reyes | ........................... | 128/849 |

* cited by examiner

*Primary Examiner* — Michael Brown
(74) *Attorney, Agent, or Firm* — Schwegman Lundberg & Woessner, P.A.

(57) ABSTRACT

Fluid collection pouches and surgical drapes for use in surgical procedures are described. The described fluid collection pouches can be configured in some cases to define a region of greater depth of the pouch beneath a patient's limb extending through the pouch on the lateral side of the limb than on the medial side. In some cases, the fluid collection pouches can be configured to define an upper surface with a region that extends at a greater height above a patient's limb extending through the pouch on the lateral side of the limb than on the medial side.

13 Claims, 3 Drawing Sheets

FLUID COLLECTION APPARATUS

CLAIM OF PRIORITY

This patent application claims the benefit of priority of U.S. Provisional Patent Application Ser. No. 61/552,254, entitled FLUID COLLECTION APPARATUS, filed on Oct. 27, 2011, which is incorporated by reference herein in its entirety.

BACKGROUND

The present invention relates generally to methods and apparatus for collecting fluids during surgical procedures; and more particularly relates to such methods and apparatus particularly adapted for surgeries on a patient's joint.

While the inventive fluid collection methods and apparatus can be used with many forms of orthopedic surgery, the present disclosure primarily addresses the use of such methods and apparatus in an example application that can particularly benefit from the teachings herein, surgery on the knee, of which one common example is arthroscopic surgery on the knee.

As of the present time, many surgeries on joints are performed arthroscopically. The most common joints subject to such surgery include the knee, elbow, shoulder wrist, foot, ankle and hip. In such surgeries, typically an arthroscope is inserted into the joint through one small incision, and surgical instruments are inserted through a second incision. In most cases, an optic fluid is employed to continuously flush the joint while it is being examined and operated upon. The fluid used in such surgery must exit the body, and typically exits from one of the incisions made to conduct the surgery. It then drips or flows down the exterior of the joint, where it must be collected in order to maintain a clean, sanitary, and functioning surgical area.

To this end, various arthroscopy fluid pouches have been developed wherein the fluid drips or flows into the pouch from the joint, and the fluid is then suctioned from the bottom of the pouch through an exit port or nipple connected to a hose which in turn is connection to a suction pump. In many cases, these arthroscopy fluid pouches are integrated with a surgical drape that, in conjunction with an integrated fluid pouch, provides a fluid barrier around the joint and a collection area for the fluids.

Many forms of these pouches have been developed over the years to address the difficulties of such fluid collection during surgery, but these conventional arthroscopy fluid pouches still suffer from one or more deficiencies in actual use. One common problem with such pouches in knee surgery, for example, is that they inhibit movement of the limb during the surgery. Another problem of many of these pouches is that they can get pinched, folded, or re-shaped during surgery so that they less efficiently perform their fluid collection function, and can permit fluid to spill over the top perimeters of such pouches and create messy, or unsanitary, or otherwise undesirable conditions for the surgery. Another problem found with some prior art fluid collection pouches intended for use in surgery on the knee is that they are designed for use, or are more efficacious for use, when a patient undergoing the arthroscopic knee surgery is positioned so that their lower leg hangs off of the end of the operating table, such as the position depicted in FIG. 1 of U.S. Pat. No. 4,974,604. However, today, many surgeons prefer to conduct such surgery with the patient in a supine position. The supine position exacerbates the aforementioned fluid collection problems, and the problems found in the pouches in the prior art.

SUMMARY OF THE INVENTION

The fluid collection pouches and surgical drapes in accordance with the present invention can include one or more multiple novel structures or features, as described herein. In many embodiments, the fluid collection pouches will be configured with an asymmetrical bottom contour to define a region of greater depth of the pouch beneath a patient's limb extending through the pouch on the lateral side of the limb than on the medial side. And in many embodiments, the fluid collection pouches will be configured with an asymmetrical top perimeter configured to define an upper surface with a region that extends at a greater height above a patient's limb extending through the pouch on the lateral side of the limb than on the medial side (when the patient and leg are in a supine position). In some of those embodiments, this region of greater height will be achieved by an extension region extending above the contours defining the majority of the surface defining the upper perimeter of the pouch. In some cases, this form of extension region will be implemented to provide an offset or discontinuity between portions at the upper (proximal) extent of the pouch.

In many embodiments, fluid collection pouches, and surgical drapes including such pouches, will preferably include a reinforcing member (or members) extending around the top perimeter of the fluid collection pouch. Preferably, the reinforcing member(s) will be encased retained within a sleeve, or otherwise bonded (such as by adhesive or some other form of attachment) proximate the upper perimeter of the pouch. In some examples, this reinforcing member will be pliable, and may be deformable, such as a metal wire or strap. The material for such a wire may be stainless steel, or another metal suitable for, and approved for, use in a sterile surgical environment. As will be apparent to those skilled in the art having the benefit of this disclosure, however, other types of material, such as flexible synthetic materials may be used to establish support and structure proximate the upper perimeter of the pouch.

In many embodiments, the surgical drape will be formed with a pouch which is asymmetrical relative to its placement on the patient's limb. Specifically, the portion of the pouch extending to the lateral, or "outside," of the patient's limb (i.e., in the case of a knee, the portion of the pouch extending to the little toe side of the leg) will have a larger dimension than the portion extending to the opposite, relative "inside," of the limb. Because this outside portion will typically be the lower side during the surgical operations, it is preferable to have a larger area to receive fluids, and thereby help avoid spillage of those fluids.

In some preferred embodiments, the upper perimeter will be formed with a discontinuity in what would otherwise represent a continuous curved elliptical shape. The discontinuity can serve to provide additional structure in support to the outer region of the pouch (as described in more detail below). In some embodiments, the top perimeter on the outer area of the pouch is lengthened and rejoined to the underlying surgical drape at a place above where the top perimeter of the inner area of the pouch joins the drape.

BRIEF DESCRIPTION OF THE DRAWINGS

FIGS. 3A-B depict the construction of the fluid collection pouch of the surgical drape of FIGS. 1 and 2; wherein FIG. 3A depicts the pattern for the material used to form the fluid collection pouch in accordance with one method of manufacture of the pouch; while FIG. 3B depicts the resulting patterned sheet of material;

EXAMPLE EMBODIMENT

The fluid collection apparatus of the present invention can be adapted for any orthopedic surgery that would benefit from fluid collection. As noted earlier herein, one example environment in which the present methods and apparatus have particular applicability is that of arthroscopic surgery of the knee, and an example configuration for a surgical drape and associated fluid collection pouch for use in such surgery is described herein. Those skilled in the art will recognize that surgical drapes in accordance with the teachings herein may be adapted as necessary for use with other surgical procedures. Minor modifications to optimize the drape for such other procedures will be apparent to persons skilled in the art having the benefit of this disclosure.

In the description of the invention that follows, the use of the term "proximal" refers to being closer to the patient's torso, and the term "distal" refers to being closer to the patient's foot. The terms "outer" and "lateral" are used to refer to the outer side of the body or a limb thereof; for example, when referring to the leg, referring to the side of the leg bearing the little toe. Analogously, the terms "inner" and "medial" are used to refer to the inner side of the body or a limb thereof; for example, when referring to the leg, referring to the side of the leg bearing the big toe. These terms are consistent with common usage, such as reference to the "inner thigh" or "outer thigh."

In one preferred implementation, the fluid collection apparatus of the present invention is implemented as a surgical drape, wherein the fluid collection pouch is formed in combination with surgical sheeting, which includes one or more layers of sheeting material. Alternatively, it would be possible for the described fluid collection pouch to be constructed and used as a separate component not physically attached to such sheeting. The sheeting material itself, exclusive of the pouch, will typically be formed of composite sheeting, which may be of any of multiple constructions known in the art. Additionally, such sheeting may not have a uniform cross-section across its entire dimension. For example, conventional surgical drapes will often include multiple layers in the sheeting closer to the surgical site, with one or more layers intended to repel fluids as well as one or more additional layers configured to absorb fluids that are not repelled. Additional sheeting layers may be present to optimize patient comfort and/or to assist in retaining surgical instruments. However, at locations remote from the surgical site, the sheeting may include a lesser number of layers, and potentially only a single layer.

Figure 1:
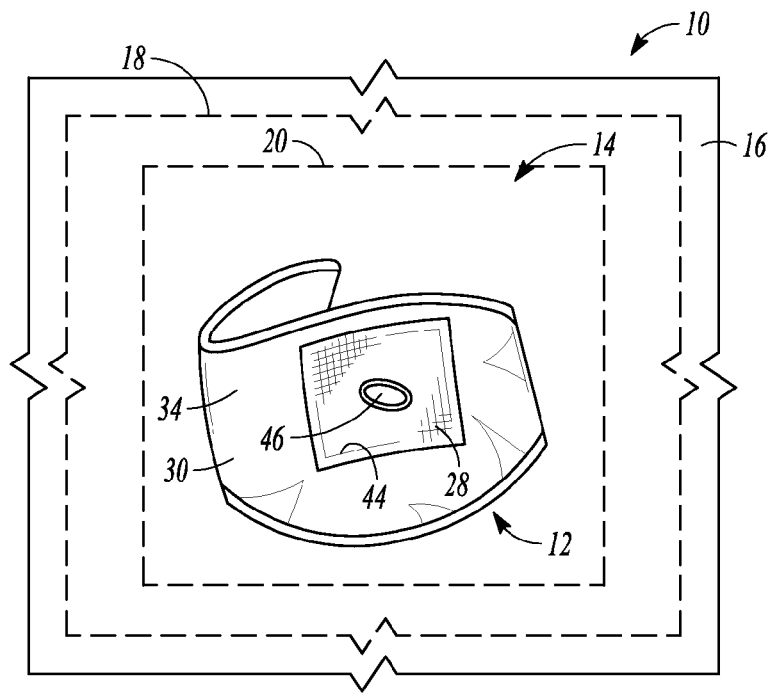
FIG. 1 depicts an example surgical drape including a fluid collection pouch in accordance with the present invention.
Figure 2:
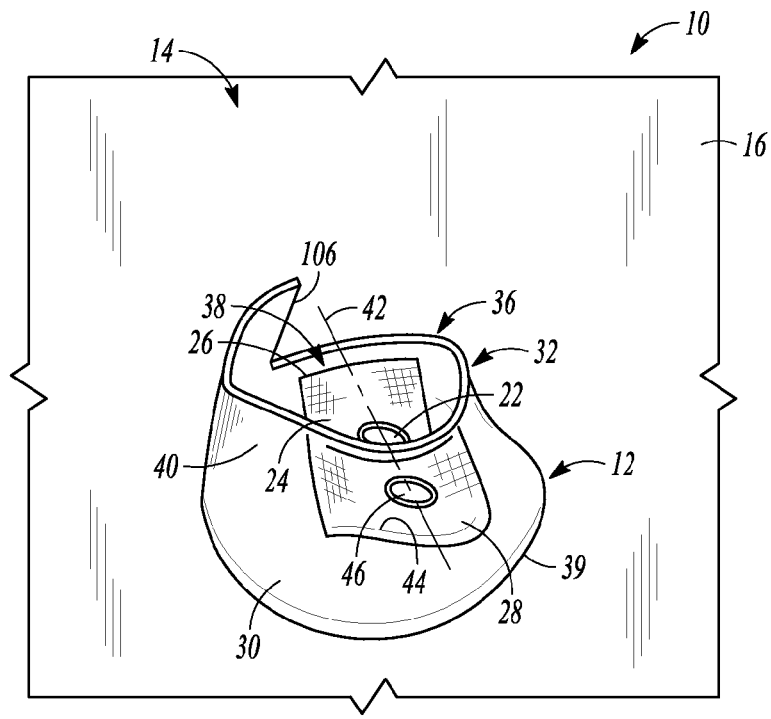
FIG. 2 depicts the surgical drape prototype of FIG. 1 with the pouch in an opened state.

Referring now to FIGS. 1 and 2, these Figures depict an example surgical drape 10, including composite sheeting 14 and fluid collection pouch 12. In FIG. 1, fluid collection pouch 12 is a generally folded position relative to composite sheeting 14; while in FIG. 2, fluid collection pouch 12 is opened somewhat to show the enclosure defined by fluid collection pouch 12. The composite sheeting portion 14 of drape 10 includes at least three layers 16, 18, 20 that are bonded together in a conventional construction. The size and configuration of sheeting 14 may be of any configuration desired, from a simple rectangular shape to more complex patterns.

Fluid collection pouch 12 is formed of a material effectively impermeable to fluids of the type presented by surgery, such as polyethylene. Fluid collection pouch 12 is bonded with an aperture therein (42 in FIG. 3B) surrounding an aperture 22 in composite sheeting 14, which allows passage of the patient's leg into the pouch. This bonding may be through use of a suitable adhesive, for example. Accordingly, in this embodiment one surface of pouch 12 becomes an integral portion of the sheeting portion 14 of drape 10.

In some embodiments, the sheeting material defining the leg aperture 22 will be an elastomeric material that will engage a first location on the patient's leg, for example the thigh, to form a fluid dam, and may include cuffs or other edge finishing that assists in forming a fluid dam around the leg. In some alternate constructions the elastomeric material may be an insert 26 of elastomeric material attached to fluid collection pouch 12, which is then attached to composite sheeting 14.

Additionally, a second such insert 28 defining an aperture 46, again preferably formed of an elastomeric material, is secured adjacent an aperture 44 in distal portion 30 of fluid collection pouch 12 to sealingly engage the patient's leg as it extends out through insert 28. By this construction, the elastomeric material 46 surrounding and defining aperture 22, as well as insert 28 defining aperture 44, are each configured to sealingly engage a leg passing therethrough, to provide fluid isolation around the portion of the leg extending through collection pouch 12, such that all fluids proximate the operating site are retained within pouch 12. As will be apparent to those skilled in the art, a patient's leg will extend approximately along an axis 42 extending through apertures 22 and 46. This axis 42 will be most apparent when the patient is in a supine position, with the knee unflexed. Axis 42 extends between and defines the medial and lateral sides of the patient's leg, and also of the fluid collection pouch (whether the pouch is in place on the patient or is separate therefrom).

Referring now particularly to FIG. 2, that figure illustrates fluid collection pouch 12 as it is been expanded from the folded or flat position of FIG. 1 to a position approximating that it would have when in place on a patient's leg. Fluid collection pouch 12 includes a top perimeter 32; a continuous side portion, indicated generally at 34; and a bottom surface indicated generally at 39. As noted above, a relatively proximal portion of the pouch, indicated generally at 36, is bonded to composite sheeting 14 with an aperture therein (42 in FIG. 3B) surrounding aperture 22, and forms a proximal portion 38 of the collection pouch 12; while an opposite portion of the pouch, indicated generally at 40, forms a distal portion of the collection pouch 12. Apertures 22 and 46, in proximal portion 38 and distal portion 40, respectively, are configured in a conventional manner to permit a human leg to pass therethrough, so that when in position, the knee is positioned within an area defined by top perimeter 32. As described in more detail later herein, a substantial portion of top perimeter 32 of fluid collection pouch 12 will be supported by a structural element, preferably a deformable member.

Referring now to FIGS. 3 A-B, these figures depict additional aspects of the construction of this example embodiment of fluid collection pouch 12. Another feature of the depicted example embodiment is an asymmetrical curve to the bottom portion (or surface) (39 in FIGS. 1 and 2) of fluid collection pouch 12. In contrast to prior art structures, as described earlier, the depicted embodiment includes a structure providing the described asymmetrical curve to the bottom portion resulting in differing "depths" to the pouch along its length, with a greater depth and volume to the pouch on the distal side of a centerline through the pouch, when viewed in profile (such as a line extending across the knee and generally perpendicular to the knee); and this region of greater depth and volume will be on the lateral side of a patient's leg when in an operative placement on the patient.

Figure 3A:
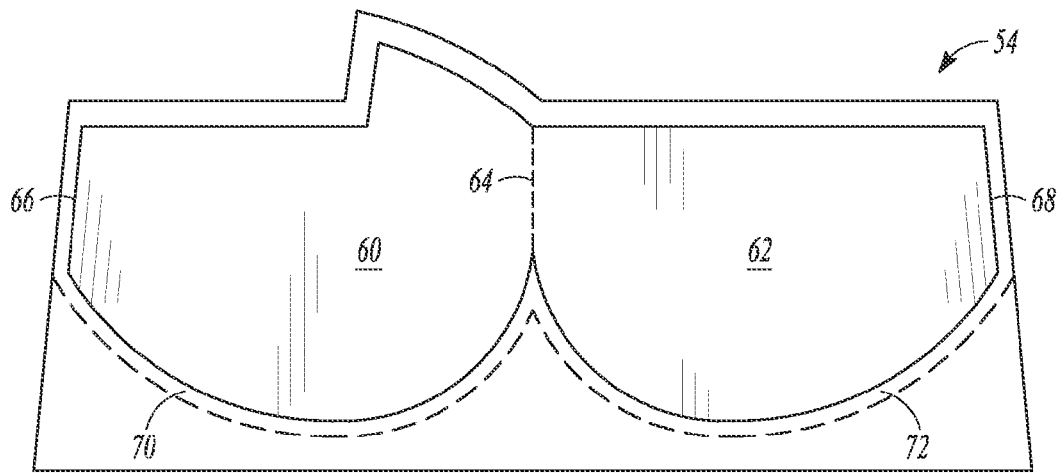

This conformation can be seen in the pouch pattern 54 depicted in FIG. 3A. The patterned sheet of material 52 of FIG. 3B formed from the pouch pattern 54 of FIG. 3A, and further includes apertures 42, 44 through which a patient's leg will pass. Pouch pattern 54 includes the forms for two opposing surfaces 60, 62 of the pouch that will be formed by folding the patterned material relative to centerline 64 and bonding the then-aligning surfaces (66 and 68; and 70 and 72) to one another to form a receptacle and to thereby define the pouch. The patterned material surface corresponding to pattern surface 60 will be bonded to the drape to generally form the proximal surface of the drape which will extend around the thigh of the patient. The patterned material portion corresponding to pattern surface 62 will form the distal portion 40 of the pouch which will extend around the patient's lower leg.

Pouch pattern 54 clearly depicts the asymmetrical curve that will be applied to the patterned material by surfaces 70 and 72. In this example, the surfaces 70, 72 defining the bottom contour of the pouch have a constantly varying radius along their entire length. In other examples utilizing an asymmetrical contour to define the pouch, some portion of the bottom contour might be linear or formed with a constant radius, with only a portion of the surface(s) defining the bottom contour of the pouch having a constantly varying radius. Alternatively, other configurations may be used to form a pouch that will have a depth below the patient's leg that expands in transition from the medial side of the leg axis (42 in FIGS. 2 and 5). For example, such a bottom might have a region of a linear transition extending downwardly relative to the leg axis 42 as the surface extends from the medial side to the lateral side.

Referring again to the disclosed embodiment, the asymmetrical curve defined at 70 and 72 may be clearly seen by examining each profile between centerline 64 and the boundaries at 66 and 68 that will be bonded together to form the opposite extent (relative to centerline 36) of the completed pouch. The result of this configuration is that collection pouch 12, when viewed in profile from a distal perspective (form the direction of the patient's feet), will have a bottom surface 36 with a shape defined by an arcuate surface with an increasing radius in the direction approaching the surfaces that define the relatively medial side of the pouch (i.e., towards lines 66 and 68), when in an intended operative placement. In other words, the shape is generally one of a French Curve, and thus has a shape generally comparable to that of the well-known Nike Swoosh™, as can be seen generally in FIGS. 3A and B. In more technical terms, the shape can generally be thought of as roughly comparable to the arc of a horizontal elliptical from a point approximating 70° to 250°.

Figure 3B:
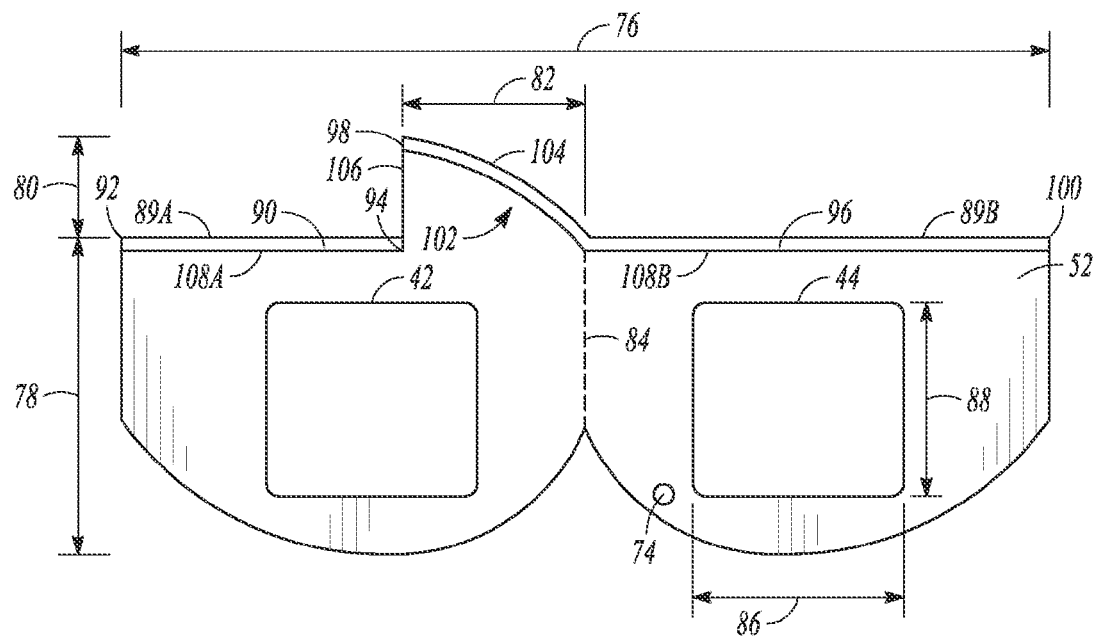

As shown in FIG. 3B, the exit port 76 is placed on the outer or lateral side and proximate the deepest portion of the pouch. The precise positioning of the exit port 76 provided will vary depending upon the precise configuration selected for bottom portion 12. The objective of the positioning is to place exit port 76 on the outer (lateral) side of pouch 12, which will be the lower side of the pouch during at least the majority of an arthroscopic procedure; and at a place along the curve that will be proximate the lowermost point of the bottom surface curve during the procedure. This conformation also improves drainage from the pouch relative to that experienced with at least some, if not all, prior art configurations. As will be apparent to those skilled in the art, a conventional port fitting (not illustrated) will be coupled proximate exit port 76 to facilitate coupling of a drain or suction hose to fluid collection pouch 12.

As will be apparent to those skilled in the art, the specific shapes and dimensions of the surfaces defining fluid collection pouch 12 may be adapted to achieve a particular desired capacity and opening around the surgical site. In the disclosed embodiment, patterned material has a generally planar majority upper surface 89a, 89b, with an extension section extending therefrom. In this example, the extension section is in the form of an upwardly extending "fin" section, defined by a curvilinear surface 104 and a generally linear surface 106. This fin section 102 will form the uppermost proximal extent of fluid collection pouch 12 on the lateral side of the patient's leg. Thus, when the patterned material is secured to the composite sheeting, as depicted in FIGS. 1 and 2, the portion having the fin section will be bonded to the sheeting, with the fin portion oriented to be on the lateral side of the patient's thigh. Thus, the material 52 in the depicted orientation is configured to be secured to sheeting material for use on a patient's left leg. If the pattern were turned over, then it would be positioned to be secured to underlying sheeting for use on a patient's right leg (as depicted in FIGS. 1 and 2).

As one example construction, the patterned sheet of material 52 of FIG. 3B can have a total length 76 between approximately 44 and 50 inches. For an example with a length of approximately 50 inches, the following additional dimensions have been found to be satisfactory. A maximum depth 78 relative to top surface 89 of approximately 15.5 inches, with the "fin" section 102 having a height 80 relative to top surface 89 of approximately 7 inches, and a horizontal dimension (as depicted) 82 of approximately 9 inches. Apertures 42 and 44 can each be approximately 9 inches on each side; though in some embodiments, aperture 44 may be slightly smaller (for example, 8 inches in at least one dimension), since it needs to accommodate only the patient's calf, rather than the thigh.

FIG. 3B also depicts placement of reinforcing members 108a, 108b, extending along nominal upper surfaces 89a, 89b, and continuing along curvilinear surface 104 of fin section 102. Reinforcing members 108a, 108b, will preferably be coupled to one another proximate points 92 and 100, to effectively form a single continuous reinforcing member 108. In some embodiments, a single reinforcing member will be used and will be attached to the patented pouch material after it has been folded and bonded to form the pouch contour. Reinforcing member(s) 108 can be bonded (through adhesive or another process) to patterned material 52; and/or in some cases may be encased within a channel (112 in FIGS. 4 and 5) in material 52, as may be formed by folding over and sealing a flap of material 52 to surround reinforcing member(s) 108. In currently preferred examples, when the material defining pouch 12 is secured to composite sheeting, the material will be bonded to the sheeting not only around aperture 42, but also along at least a portion of fin section 102, such as linear surface 106, and along at least a portion of upper surface 89a.

Reinforcing member 108 can also extend along the entire upper surface of the patterned material (i.e., also along linear portion 106 of fin section 102, in the depicted example);

though such is not needed, and in some processes may complicate the manufacturing process somewhat. As can be appreciated from review of FIG. 3B as well as FIGS. 1 and 2, the dimension of linear surface 106 of the "fin" portion 102 establishes a longitudinal offset between a first end of reinforcing member 108, at location 98 (proximate the "top" of fin section 102), which will extend from the lateral side of the limb, relative to the second end of reinforcing member 108, at location 98, which will extend from the medial side of the limb. This longitudinal offset, which in this example will be proximally located adjacent the patient's thigh, provides the previously described greater depth and volume of fluid collection pouch 12 on the lateral side of the patient's leg, relative to the medial side. This discontinuity or offset in top perimeter 32 (adjacent surface 106 in the depicted example) is present whether or not reinforcing member 108 is continuous around top perimeter 32.

As discussed above, the reinforcing member will be pliable, and preferably deformable, such that the material resists deformation of top perimeter 32, but can be shaped deliberately by medical personnel as part of the surgery to hold a desired shape. A metallic wire, such as stainless steel wire, retained within channel (112 in FIGS. 4 and 5) is one example of a desirable reinforcing member. For some examples, plastic coated wire of approximately 24 gauge has been found to be satisfactory. In some embodiments, it may be desirable to have a reinforcing member that offers greater resistance to deformation of top perimeter 32 in the distal portion 40 as compared to the top perimeter 32 in the proximal portion 38. This non-uniform resistance to deformation around the periphery can be achieved by a variety of mechanisms, including having a reinforcing member or a reinforcing member assembly that is of a different material and/or dimension in distal portion 40 than in proximal portion 38. Alternatively, multiple reinforcing members (such as, for example, multiple metal wires) might be used in distal portion 40, with only a single reinforcing member placed in proximal portion 38. However the reinforcing member is constructed, it will preferably be a continuous assembly from a first end at a relatively proximal position when in use (i.e., a "proximal end") to a second end at a relatively distal position when in use (i.e., a "distal end").

Figure 4:
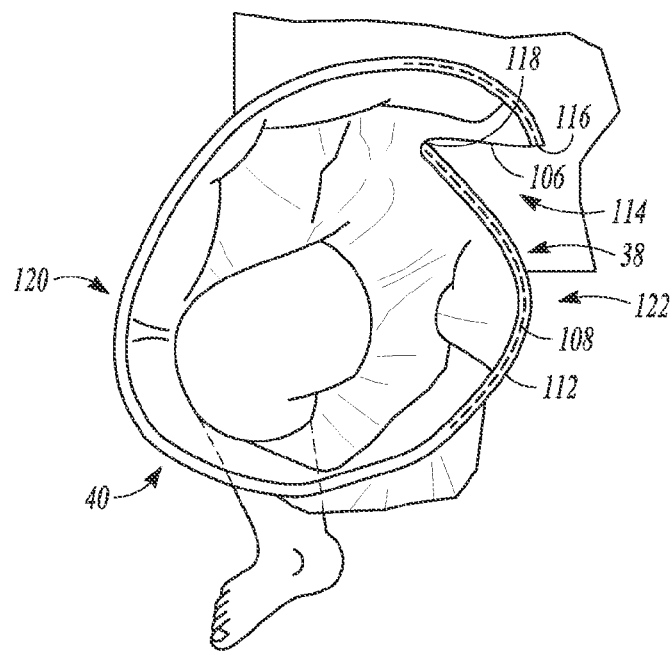
FIG. 4 depicts a surgical drape including a fluid collection pouch in an operating placement, disposed on a patient's leg while the knee is flexed with the patent in the supine position (thus, the foot will be on the underlying surgical table (not depicted)), as will typically occur during a surgical procedure.
Figure 5:
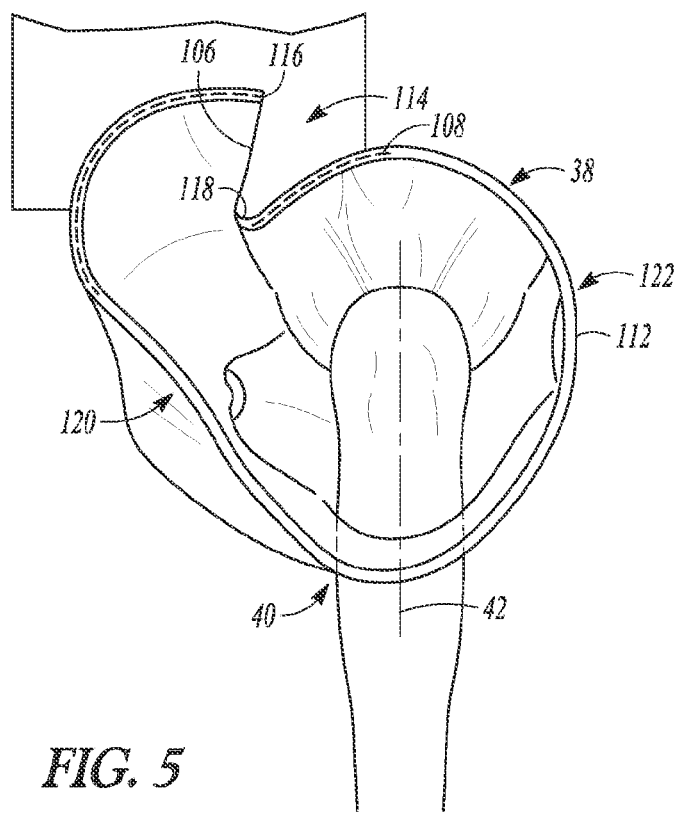
FIG. 5 depicts the surgical drape placement of FIG. 4 from an alternate view.

As depicted in FIGS. 4 and 5, those figures depict an example embodiment of a surgical drape as described herein, in position to fluidically isolate a patient's knee, such as for arthroscopic surgery on the knee. In these Figures, for clarity, only a portion of composite sheeting 14 is shown. To place the drape in position, the patient's foot of the patient is first passed through the opening 22 in the proximal portion and then the opening 44 in the distal portion. The drape is then moved further up the patient's leg, until the opening 22 in the proximal portion fits about the patient's thigh, and the opening 44 in the distal portion 30 fits about the patient's leg below the knee. The shaping of the pouch is assisted by deformable reinforcing member 108 secured proximate top perimeter 32.

As noted above, some embodiments also rely on an upper perimeter that is discontinuous relative to a continuous elliptical curve, as depicted generally at 114. This can be achieved by different mechanisms. For example, as depicted in the referenced figures, it can be seen that the top perimeter 32 of collection pouch 12 has a proximal end 116 and a relatively distal end 118 that do not join one another. In this example embodiment, this discontinuity is formed in part by surface 106 which extends between ends 116 and 118. The relatively distal end 118 of top perimeter 32 of fluid collection pouch 12 is formed with distal region 40 of the fluid collection pouch; while proximal end 116 of top perimeter 32 of pouch 32 is formed with the proximal region 38 of fluid collection pouch 12. Ends 116 and 118 are proximate one another adjacent the patients thigh, but are offset from one another by a short distance (preferably a few inches). Thus, the relatively proximal and distal ends 116, 118, respectively, of top perimeter 32 will often essentially overlap one another proximate the patient's thigh. The overlapping structure is believed to give added strength to the outer (lateral) side of the collection pouch that is under the most stress during surgery. The overlapping section is also believed to reduce the risk of the collection pouch from failing by either collapsing or kinking during surgery. Thus the structure provides improved fluid collection and retention performance of fluid collection pouch 12. In other embodiments, there may be a connection between the two sections of the pouch surface perimeter, and in such cases there will typically be a dogleg or other transition region between the arc of the perimeter of the lateral portion of pouch 12 (indicated generally at 120) relative to the arc of the perimeter of the medial portion (indicated generally at 122).

As noted above, in some embodiments, it will be desirable to have a greater volume of the pouch on the outer (lateral) side of the patient's leg, than on the inner (medial) side. Because that outer side will often be the lower side during certain stages of the surgical operations, a greater volume on this outer side will better facilitate capture and retention of fluids within the pouch. In the depicted example, this difference in volume is facilitated by the longer arc 120 of top perimeter 32 on the lateral side, proximally terminating at location 116; as compared to the shorter arc 122 on the medial side, terminating at location 118. In this embodiment, the additional length of top perimeter 32 that ends at the proximal end portion 116 (attached to the sheet portion at a portion relatively proximal position, relative to the location 118 at which the distal portion of top perimeter 32 is attached to the sheet portion of the drape), helps provide stability to collection pouch 12, such that during surgery applying pressure against collection pouch 12, or the unintentional deformation of the collection pouch 12 will not readily lead to spillage or leakage of arthroscopy-related fluid as was the case with prior art designs.

In embodiments as depicted in the accompanying figures, which include both the unequal lengths to the outer and inner perimeters defining fluid collection pouch 12; and the asymmetrical shape of bottom portion 29, those features enable pouch 12 to be shorter than pouches of conventional surgical drapes.

Many additional modifications and variations may be made in the techniques and structures described and illustrated herein without departing from the spirit and the scope of the present invention. Accordingly, the present invention should be clearly understood to be limited only by the scope of the claims and equivalents thereof.

We claim:

1. A fluid collection apparatus suitable for collecting fluid during arthroscopy knee surgery, comprising:
    a first portion of material forming a drape; and
    a second portion of material extending from said drape in order to form a pouch, where said pouch comprises at least a top perimeter, a proximal side portion, a distal side portion, an outer side portion, an inner side portion, and a bottom portion;
    wherein the proximal side portion of said pouch contains a first opening and the distal side portion of said pouch contains a second opening, and wherein said first and second openings are suitable for permitting passage of a human leg therethrough, and wherein said proximal side portion is suitable for fitting about a portion of a human leg above the knee, and said distal side portion is suitable for fitting about a portion of a human leg below the knee;

wherein the top perimeter has a distal end and a proximal end, and wherein the top perimeter forms a generally elliptical configuration that is asymmetrical between the medial side and the lateral side when the fluid collection apparatus is placed on a patient's leg in an operating configuration.

2. The fluid collection apparatus of claim 1, wherein the structure defining the first opening in said proximal side portion and the structure defining the second opening in said distal side portion, are each configured to provide a substantially leakproof seal around the patient's leg.

3. The fluid collection apparatus of claim 1, wherein the top perimeter forms a generally elliptical shape, except that the arc of the lateral proximal portion of said top perimeter is longer and further from the knee when positioned for surgery than the medial distal portion of said top perimeter.

4. The fluid collection apparatus of claim 1, wherein the bottom portion of the pouch includes at least a portion defining an arc with a continually varying radius, and with the area of the relatively greater radius extending to the lateral side of the patient's leg.

5. The fluid collection apparatus of claim 1, wherein the proximal end of said top perimeter attaches to said drape at a first location that is proximate, but offset from, a second location where the relatively distal end of said top perimeter attaches to said drape, such that when the fluid collection apparatus is placed on a patient's leg, the top perimeter defines a first length on the medial side of the patient's leg and a second length greater than the first length on the lateral side of the patient's leg.

6. A surgical drape for use doing arthroscopic knee surgery, comprising:
a sheet portion, configured to cover at least a portion of a patient's body; and
a pouch, secured to the sheet portion, the pouch formed of a material capable of retaining fluids, and comprising,
an upper perimeter, and
a retention member secured to the upper perimeter, the retention member formed of a pliable material that is capable of being deformed;
wherein both the sheet portion and the pouch portion are joined together to form a first surface, and wherein that first surface comprises a first aperture configured to engage a patient's thigh; and
wherein the pouch portion further comprises a second aperture configured to engage a patient's leg below the knee; and
wherein the pouch has an upper perimeter surface having a greater dimension on the lateral side of the patient's leg than on the medial side of the patient's leg.

7. The surgical drape of claim 6, wherein the pouch further comprises a bottom surface, and wherein the bottom surface is defined by an asymmetrical curve of varying radius.

8. The surgical drape of claim 6, wherein the upper perimeter of the pouch includes a discontinuity.

9. The surgical drape of claim 8, wherein the retention member has a first end at a first side of the discontinuity and a second and at a second side of the discontinuity.

10. The surgical drape of claim 9, wherein the upper perimeter and the retention member are configured to allow the first end and the second end of the retention member to overlap one another when the drape is positioned on a patient.

11. A surgical drape for use during knee surgery, comprising:
a sheeting portion; and
a fluid retentive pouch attached to the sheeting portion and configured to extend around a patient's knee, the pouch having a first aperture configured to extend around the patient's thigh, and a second aperture configured to extend around the patient's calf, wherein the first and second apertures generally define the axis of a leg through the pouch when the pouch is in place on a patient;
wherein the pouch further includes a lower surface that transitions from a first depth below the axis of a leg through the first and second apertures on the intended medial side of the axis to a second, greater, depth below said axis on the intended lateral side of the axis, to define a greater depth to the pouch beneath the leg on the lateral side than the medial side.

12. The surgical drape of claim 11, wherein the pouch further comprises a top perimeter that transitions from a first distance above said axis on the intended medial side of said axis to a second, greater, distance above said axis on the intended lateral side of said axis.

13. The surgical drape of claim 11, wherein the pouch further comprises a deformable member secured proximate the top perimeter of the pouch, wherein the deformable member has a first end extending from said medial side of said axis, and a second end extending from the lateral side of said axis, and wherein the second end extends to a location that will be proximally above the first end when the surgical drape is in place on a patient.

* * * * *